United States Patent [19]

Demarest

[11] Patent Number: 4,886,070

[45] Date of Patent: Dec. 12, 1989

[54] METHOD OF IN VIVO CALIBRATION OF A PRESSURE SENSOR

[75] Inventor: Philip C. Demarest, Pine Brook, N.J.

[73] Assignee: Thermometrics, Inc., Edison, N.J.

[21] Appl. No.: 192,604

[22] Filed: May 11, 1988

[51] Int. Cl.[4] .............................................. A61B 5/02
[52] U.S. Cl. ..................................... 128/675; 128/748
[58] Field of Search ............................... 128/672–675, 128/748; 73/4 R

[56] References Cited

U.S. PATENT DOCUMENTS

| | | | |
|---|---|---|---|
| 3,088,323 | 5/1963 | Welkowitz et al. | 128/675 X |
| 3,550,583 | 12/1970 | Chiku et al. | 128/675 |
| 3,703,099 | 11/1972 | Rouse | 128/673 X |
| 3,710,781 | 1/1973 | Hutchins et al. | 128/675 |
| 3,724,274 | 4/1973 | Millar | 128/675 X |
| 3,748,623 | 7/1973 | Millar | 73/782 X |
| 3,831,588 | 8/1974 | Rindner | 128/675 |
| 4,023,562 | 5/1977 | Hynecek et al. | 128/675 X |
| 4,191,193 | 3/1980 | Seo | 128/675 |
| 4,274,423 | 6/1981 | Mizuno et al. | 128/675 |
| 4,342,218 | 8/1982 | Fox | 128/673 X |
| 4,407,296 | 10/1983 | Anderson | 128/675 |
| 4,554,927 | 11/1985 | Fussell | 128/670 |
| 4,610,256 | 9/1986 | Wallace | 128/673 X |
| 4,658,829 | 4/1987 | Wallace | 128/672 |
| 4,672,974 | 6/1987 | Lee | 128/673 |
| 4,760,730 | 8/1988 | Frank et al. | 73/4 R |

Primary Examiner—Angela D. Sykes
Attorney, Agent, or Firm—Lerner, David, Littenberg, Krumholz & Mentlik

[57] ABSTRACT

An improved miniature, in vivo, pressure sensor is disclosed which comprises a housing having an internal chamber adapted to be connected to a conduit for varying the pressure therein; a piezoresistive element positioned in the chamber and adapted to be connected to a circuit for sensing changes in the resistance of the piezoresistive element; a pressure responsive element carried by the housing and having an inner portion and an outer portion, the inner portion being exposed to the pressure extant in the interanl chamber and the outer portion being exposed to ambient pressure conditions outside of the housing; and a coupling device releasably sistive element in such a manner that when equal pressures are concurrently applied to the inner and outer portions of the pressure responsive element, the pressure responsive element applies a predetermned load to thre piezoresistive element and when unequal pressures are concurrently applied to the inner and outer portions of the pressure responsive element, the load applied by the pressure responsive element to the piezoresistive element correspondingly changes. A method fo checking the calibration of the pressure sensor and recalibrating it, when necessary, while it remains in an in vivo measurement site, is also disclosed. The method includes, inter alia, the steps of applying a gradually increasing unloading pressure to the pressure responsive element to decrease the predetermined load on, and output of, the piezoresistive element, and establishing the value of the unloading pressure at which the output of the piezoresistive element ceases to decrease.

4 Claims, 3 Drawing Sheets 4,886,070

METHOD OF IN VIVO CALIBRATION OF A PRESSURE SENSOR

FIELD OF THE INVENTION

This invention relates to strain gage type pressure sensors and to methods of calibrating such sensors under in vivo conditions. More particularly, it relates to strain gage type pressure sensors which permit in vivo calibration of the zero-offset due to drift, and to a method employed in calibrating such pressure sensors for such drift.

BACKGROUND OF THE INVENTION

Miniature pressure sensors or transducers mounted at the distal end of catheters are commonly used to measure internal blood pressure in patients. The pressure sensor and catheter are inserted into the subject and positioned at a measurement site of interest. Such invasive pressure sensors provide high quality signals which permit very accurate determinations of the location and extent of such problems as heart valve malformations and malfunctions.

Examples of presently known invasive pressure sensors can be found in U.S. Pat. No. 3,088,323 to Welkowitz et al, U.S. Pat. No. 3,550,583 to Chiku et al, U.S. Pat. No. 3,710,781 to Hutchins, IV et al, U.S. Pat. No. 3,724,274 and U.S. Pat. No. 3,748,623 to Millar, U.S. Pat. No. 4,023,562 to Hynecek et al, U.S. Pat. No. 4,191,193 to Seo, U.S. Pat. No. 4,274,423 to Mizuno et. al, and U.S. Pat. No. 4,554,927 to Fussell. Several of the foregoing patents show the use of temperature compensation features in association with the pressure sensors, which adjust the ultimate pressure readings to correct for inaccuracies that might otherwise be caused by temperature variations.

The present pressure sensor invention represents an improvement over the temperature-compensated and other types of pressure sensors disclosed in the aforementioned U.S. patents. It will be described in connection with a temperature-compensated pressure sensor of the type disclosed in U.S. Pat. No. 4,554,927 to Fussell, the disclosure of which patent is incorporated herein by reference. The Fussell patent is assigned to the assignee of the present invention.

The typical prior art pressure sensor includes a housing having an internal chamber. It also includes a pressure responsive element having inner and outer portions exposed respectively to atmospheric pressure conditions in the internal chamber and to ambient pressure conditions outside of the housing. In addition, a piezoresistive element is positioned in the internal chamber, and means are provided to couple the pressure responsive element to the piezoresistive element so that pressure changes outside of the housing are reflected by resistance changes in the piezoresistive element. Typically, the pressure sensor also includes a reference piezoresistance element which provides some level of temperature compensation, and compensating electrical circuitry is provided to accommodate differences in thermal coefficients of expansion which may affect the pressure responsive and temperature responsive piezoresistive elements differently.

As a result of aging characteristics of the pressure responsive element, the piezoresistive elements, circuit elements, and other construction materials, there generally are drift characteristics associated with the zero output and the gain characteristics of the pressure sensor and its allied circuitry. Accordingly, during use, it is often necessary to recalibrate the sensor to be certain that any drift that may have occurred does not result in erroneous readings. In order to recalibrate the sensor, it is necessary to establish a zero differential pressure to check for zero drift and then to apply a known, nonzero, pressure differential to check for gain drift. Such calibration is particularly difficult for devices that are capable of making in vivo measurements. The reason for this problem is that there is no way of accessing the portion of the pressure sensor which is exposed to the measurement site (i.e., the exposed surface of the pressure responsive element).

It is, therefore, a primary object of the present invention to provide an improved pressure sensor which permits calibration of its zero offset due to drift while the pressure sensor is in an in vivo location.

It is another object of the present invention to provide a method for checking the calibration of a pressure sensor while it is located in an in vivo measurement site.

An additional object of the present invention is to provide a method of recalibrating a pressure sensor while it is located in an in vivo measurement site.

Further objects and advantages of this invention will become apparent as the following description proceeds.

SUMMARY OF THE INVENTION

Briefly stated, and in accordance with one embodiment of this invention, An improved pressure sensor comprises a housing having an internal chamber adapted to be connected to a conduit means for varying the pressure therein; a piezoresistive element positioned in the chamber and adapted to be connected to circuit means for sensing changes in the resistance of the piezoresistive element; a pressure responsive element carried by the housing and having an inner portion and an outer portion, the inner portion being exposed to the pressure extant in the internal chamber and the outer portion being exposed to ambient pressure conditions outside of the housing; and means coupling the pressure responsive element to the piezoresistive element in such a manner that when equal pressures are concurrently applied to the inner and outer portions of the pressure responsive element, the pressure responsive element applies a predetermined load to the piezoresistive element and when unequal pressures are concurrently applied to the inner and outer portions of the pressure responsive element, the load applied by the pressure responsive element to the piezoresistive element correspondingly changes.

In accordance with another embodiment this invention provides, in a method of checking the calibration of a pressure sensor, which pressure sensor includes a piezoresistive element and a pressure responsive element releasably coupled to the piezoresistive element, the pressure responsive element applying a predetermined load to the piezoresistive element in the absence of a pressure differential being applied across the pressure responsive element, the steps of applying a gradually increasing unloading pressure to the pressure responsive element to decrease the predetermined load on the piezoresistive element; checking the output of the piezoresistive element while the predetermined load is being decreased; and establishing the value of the unloading pressure at which the output of the piezoresistive element ceases to decrease.

In accordance with yet another embodiment of this invention, an improved method of checking the calibration of an in vivo pressure sensor comprises the steps of: (A) Providing a pressure sensor including a housing having an internal chamber, the pressure sensor including a pressure responsive element having an inner portion and an outer portion exposed, respectively, to pressure conditions in the internal chamber and outside of the housing, a piezoresistive element positioned in the chamber, a means coupling the pressure responsive element and the piezoresistive element in such a manner that when equal pressures are applied to opposite sides of the pressure responsive element, the pressure responsive element applies a predetermined load to the piezoresistive element and when unequal pressures are applied to opposite sides of the pressure responsive element, the load applied by the pressure responsive element to the piezoresistive element correspondingly changes, the pressure sensor further including conduit means in communication with the internal chamber and leading to a location remote from the chamber, and circuit means connected to the piezoresistive element and leading to a location remote from the chamber; (B) Providing meter means having a zero adjustment control in circuit with the circuit means; (C) Prior to inserting the pressure sensor into an in vivo environment, (i) exposing both sides of the pressure responsive element to a common pressure source and setting the zero adjustment controls so that the meter means reads zero pressure output, (ii) applying a gradually increasing back pressure $P_R$ to the internal chamber while applying atmospheric pressure to the outer side of the pressure responsive element to reduce the predetermined load to zero, and recording the back pressure $P_{Ro}$ at which the output of the meter stops decreasing; (D) Inserting the pressure sensor into an in vivo environment and (i) observing the pressure value $P_D$ displayed on the meter means with the back pressure $P_R$ equal to atmospheric pressure, (ii) slowly increasing the back pressure $P_R$ until the displayed value $P_D$ stops decreasing and then recording the back pressure value $P_{Rc}$ corresponding to this point, (iii) subtracting the value of $P_{Ro}$ from the value of $P_{Rc}$ obtained in step C(ii) above to obtain the true differential pressure $P_{Dt}$ and comparing the value of $P_{Dt}$ so obtained with the value of $P_D$ observed in step D(i) above, whereby, if the values of $P_{Dt}$ and $P_D$ compared in step D(iii) are in substantial agreement, the pressure sensor and meter means can be assumed to be in calibration and, if such values are not in substantial agreement, the pressure sensor and meter means can be assumed to be out of calibration.

In accordance with yet another embodiment of this invention the meter means referred to in the preceding paragraph includes a gain control in circuit with the circuit means referred to therein and, if the values of $P_{Dt}$ and $P_D$ compared in step D(iii) of such preceding paragraph are not in substantial agreement, the method described in the preceding paragraph includes recalibrating the pressure sensor by performing the further steps of: (E) Applying two different back pressures or vacuums $P_{R1}$ and $P_{R2}$, each of which is less than the value of $P_{Rc}$ and one of which may be atmospheric pressure, to the internal chamber of the pressure sensor, observing the corresponding pressures $P_{D1}$ and $P_{D2}$ displayed on the meter means, and computing the gain factor G by the equation G equals the difference of $P_{D1}$ minus $P_{D2}$ divided by the difference of $P_{R1}$ minus $P_{R2}$; (F) Adjusting the gain control to obtain a new display pressure $P_{Dn}$ given by the equation $P_{Dn}$ equals the displayed pressure $P_D$ displayed in step F above divided by the gain G obtained in step E; and, (G) Adjusting the zero adjustment control so that the new displayed pressure $P_{Dn}$ is made equal to the true differential pressure $P_{Dt}$ determined from step D(iii) of the preceding paragraph.

BRIEF DESCRIPTION OF THE DRAWINGS

While the specification concludes with claims particularly pointing out and distinctly claiming the subject matter regarded as the invention herein, it is believed that the present invention will be more readily understood from the following description, taken in conjunction with the accompanying drawings, in which:

DETAILED DESCRIPTION OF THE INVENTION

Figure 1:
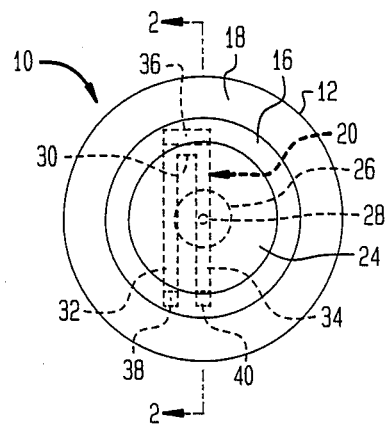
FIG. 1 is an end view of a temperature-compensated pressure sensor in accordance with the present invention.
Figure 2:
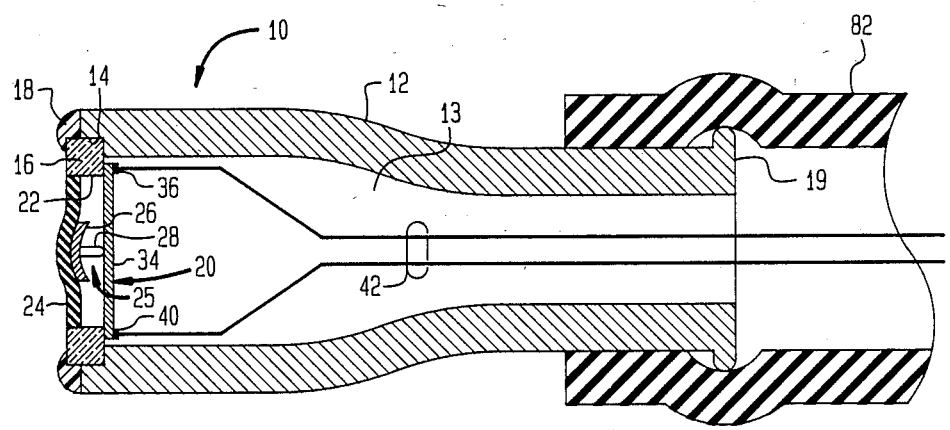
FIG. 2 is a sectional elevation view of the pressure sensor of FIG. 1, taken along the lines 2—2 of FIG. 1.

Referring now to the Figures, and more particularly to FIGS. 1 and 2 thereof, there is illustrated a temperature-compensated pressure sensor, shown generally at 10, which incorporates the principals of the present pressure sensor invention. The pressure sensor 10 includes an elongated, generally cylindrical, housing 12, preferably constructed of stainless steel or a like suitable material, which surrounds the axially extending portion of an internal chamber 13. Elongated housing 12 has an opening 14 at one end thereof in which is mounted a sensor mounting ring 16 that is preferably constructed of silicon or a similar material which matches the expansion coefficient of a sensor gage element 20. Sensor gage element 20 is mounted on ring 16 and will be described in greater detail hereinafter. The sensor mounting ring 16 is secured in the opening 14 by an epoxy fillet 18, although other suitable affixing means could be employed. The other end 19 of housing 12 is adapted to be fixedly connected to an elongate catheter 82 which is used to interconnect the pressure sensor 10 with an external metering and calibrating location when the sensor is at an in vivo measurement site.

The sensor mounting ring 16 has an opening 22 over which is sealed a pressure responsive element 24, for example a flexible diaphragm constructed of surgical grade silicone rubber or the like. Positioned between the interior of the pressure responsive element 24 and the sensor gage element 20 is a force transmitting member, shown generally at 25, which includes a force summing plate 26 and a shaft 28 integral therewith. The force transmitting member 25 should be bonded to one or the other of the pressure responsive element 24 and the sensor gage element 20, but not to both.

The shaft 28 of force transmitting member 25 is made sufficiently long so as to pre-stress the pressure responsive element 24 and to insure that the force transmitting member is in contact with, and providing an initial strain on, the sensor gage element 20 when both sides of the pressure responsive element 24 are exposed to a common pressure source, for example atmospheric pressure. Preferably, the pressure responsive element 24 and force transmitting member 25 apply about a five gram initial load on the sensor gage element 20 under such conditions of pressure. However, the amount of this initial load is not critical so long as some initial strain is applied to the sensor gage element 20 in order to facilitate the calibration to be described hereinafter.

As can best be seen in FIG. 1, the sensor gage element 20 is substantially U-shaped and includes a median or bight portion 30 and leg portions or elements 32 and 34. The sensor gage element 20 is of the piezoresistive type and is constructed such as to form a monolithic bifurcated silcon strain gage which is cut from a single site of a doped silicon crystal. An electrical contact 36 is disposed on the sensor gage element 20 at the bight portion 30 thereof; an electrical contact 38 is disposed on the sensor gage element 20 at the end of the leg portion 32 thereof; and, an electrical contact 40 is disposed on the sensor gage element 20 at the end of the leg portion 34 thereof. The electrical contacts 36–40 are coupled to a circuit which will be hereinafter described in conjunction with the illustration of FIG. 3.

The sensor gage element 20 is adhesively or otherwise fastened to the sensor mounting ring 16 and is positioned so that only leg portion 34 thereof is in contact with the shaft 28 of force transmitting member 25. As a result, when pressure acts upon the pressure responsive element 24, this force is imparted to the piezoresistive leg portion 34 of the sensor gage element 20. The other piezoresistive leg portion 32 of the sensor element 20 is not exposed to any pressure except for the ambient environmental pressure within the internal chamber 13 of housing 12. Insulated electrical leads are connected to the electrical contacts 36, 38 and 40 and are joined in a cable 42 for connection to an electrical circuit, shown generally at 44 in FIGS. 3 and 4.

Figure 3:
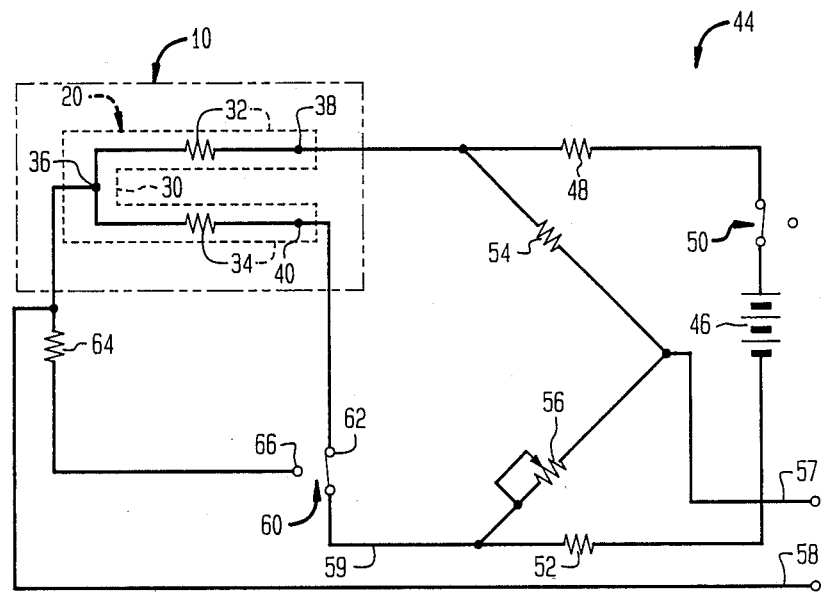
FIG. 3 is an electrical circuit that may be employed in using the pressure sensor of the present invention.

Referring to FIG. 3, the piezoresistive leg portions 32 and 34 of sensor gage element 20 are connected to electrical circuit 44 in such a manner that the leg portion 32 can serve either as a biological temperature sensor of tissue in the adjacent environment, or as a temperature compensator for the pressure sensor leg portion 34. The electrical circuit 44 comprises an essentially conventional Wheatstone bridge that includes an excitation supply 46 connected at one end thereof to a current limiting resistor 48 through an on/off switch 50, and at the other end thereof to another current limiting resistor 52. Also included in the Wheatstone bridge are fixed bridge-balancing resistor 54 and a variable bridge-balancing resistor or potentiometer 56, the latter serving to permit calibration of the Wheatstone bridge circuitry. The output signal of the Wheatstone bridge circuitry appears across a pair of conductors 57, 58.

The junction of the fixed bridge-balancing resistor 54 and the variable bridge-balancing resistor 56 is connected to the bridge output signal conductor 57. The other bridge output signal conductor 58 is connected to the electrical contact 36 that is disposed on the bight portion 30 of sensor gage element 20. The current limiting resistor 48 is connected at the end thereof which is remote from switch 50 to the junction of the fixed bridge-balancing resistor 54 and the electrical contact 38 disposed at the end of the piezoresistive leg portion 32 of sensor gage element 20. The end of the current limiting resistor 52 which is remote from the excitation supply 46 is connected to a conductor 59 which interconnects the variable bridge-balancing resistor 56 and the wiper of a double throw-single pole switch 60. One contact 62 of the switch 60 is electrically connected to the electrical contact 40 disposed on the piezoresistive leg portion 34 of sensor gage element 20. A fixed resistance 64 is connected between the other contact 66 of switch 60 and the electrical contact 36 disposed at the bight portion 30 of the sensor gage element 20.

It should be readily apparent from the foregoing discussion that a conventional Wheatstone bridge is provided with the exception that, at any given time, one or the other of piezoresistive leg portion 34 and fixed resistor 64, but not both, may be selectively switched into the Wheatstone bridge circuit 44. When the wiper of the switch 60 is in the position illustrated in FIG. 3, contacting pole 62, the piezoresistive leg portion 34 of sensor gage element 20 is in the Wheatstone bridge circuit 44 and the output across the bridge output signal conductors 57 and 58 is indicative of the pressure imparted to the piezoresistive leg portion 34 but is compensated for changes in temperature by virtue of the inclusion of the piezoresistive leg portion 32 in the bridge circuit 44. When the wiper of switch 60 is positioned to be in contact with pole 66, then the fixed resistance 64, selected to be of a suitable value, is placed in the Wheatstone bridge circuit 44 and the output across the bridge output signal conductors 57 and 58 is indicative of the ambient environmental temperature of the surroundings of the housing 12, as sensed by the piezoresistive leg portion 32 of sensor gage element 20.

As a result, an apparatus is provided which will not only provide the user with signals representative of pressure readings compensated for temperature variations but which also will selectively give signals representative of readings of environmental temperature unaffected by the effects of the pressure to be measured. Selection of the values of the current limiting resistors 48 and 52 and the fixed bridge balancing resistor 54, as well as the fixed resistor 64, depend upon the specifications of a bridge output indicating meter that receives and displays the bridge output signal and the specifications of the excitation supply 46, as well as on the resistive characteristics of the sensor gage element 20, and are well within the skill of one of ordinary skill in the art. It is contemplated that the components of electrical circuit 44 which are shown outside of the broken lines of the pressure sensor, designated at 10 in FIG. 3, will be located in some location external to the biological body in which the pressure and temperature sensor 10 is placed. However, other configurations, for example the placement of one or more of the fixed resistors 48, 52, 54 and 64 within the elongated housing 12, are also quite possible.

Figure 4:
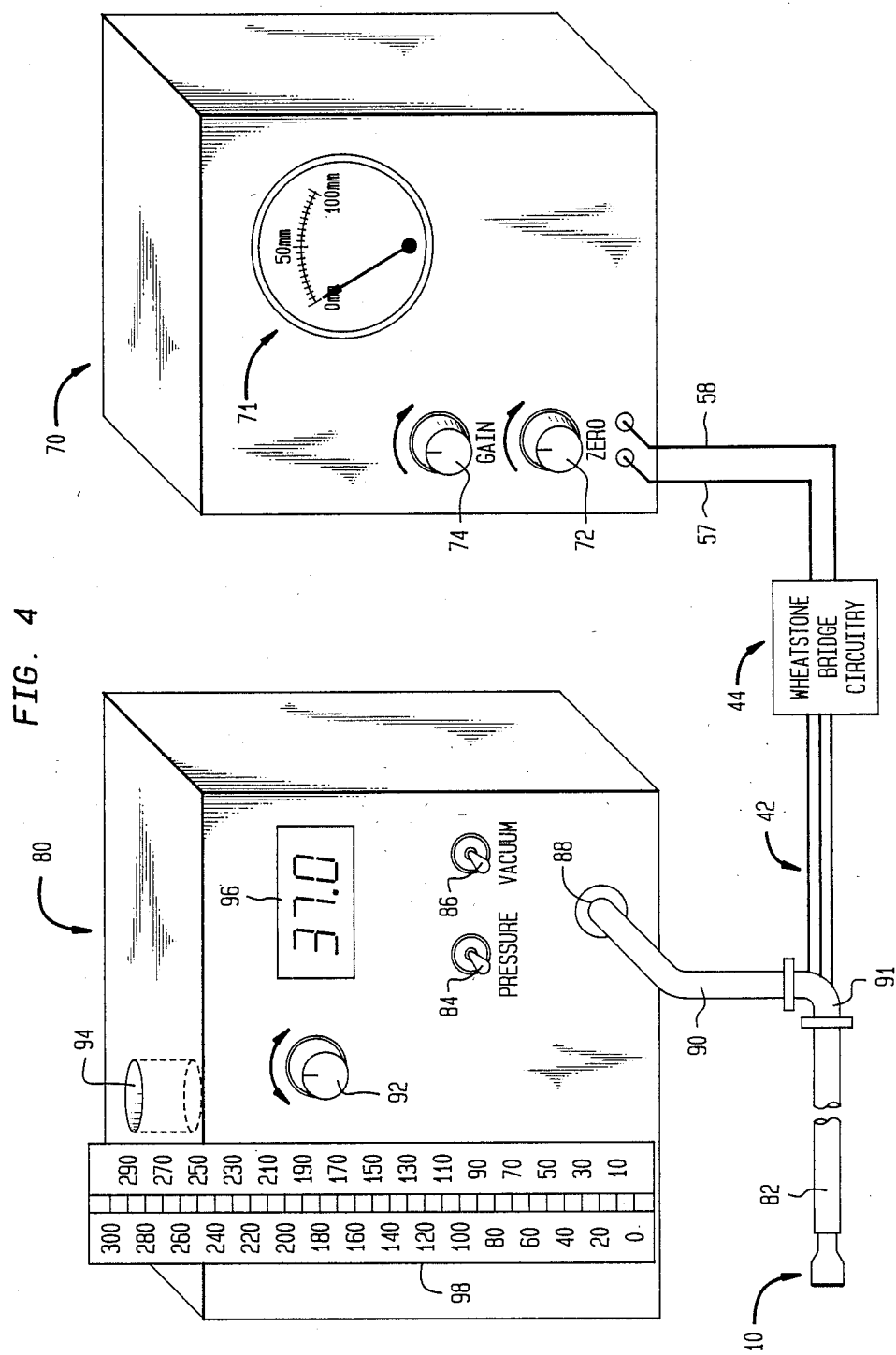
FIG. 4 is a diagramatic view of the pressure sensor connected to a calibration device and to a meter instrument that may be used in practicing the method of this invention.

Referring now to FIGS. 2 and 4, together, and before discussing the method by which the calibration of the sensor 10 may be checked and recalibrated, in accordance with this invention, it should be noted that an initial calibration procedure is utilized which involves setting the zero adjust and gain adjust values of a meter instrument, shown generally at 70, having an indicating meter 71 which displays the pressure readings of the sensor 10. For example, with both sides of the pressure responsive element 24 exposed to atmospheric pressure, a zero adjust control 72 of the meter instrument 70 is set to provide an output display, or base line value, of zero millimeters (mm) of mercury (Hg). A pressure differential of 100 mm of Hg is then applied across the pressure responsive element 24, by drawing a vacuum within the chamber 13 of the sensor 10, and a gain adjust control 74 is set to provide a display of 100 mm of Hg. An additional differential pressure (e.g., 50 mm of Hg) can be applied across pressure responsive element 24 in the same manner and the display read to verify the linearity of the pressure sensor 10. Experience indicates that the linearity of the sensor 10 is not significantly affected by aging and drift factors.

The pressure differentials used in the foregoing initial calibration procedures are provided by a calibration device or calibrator, shown generally at 80, which is capable of providing pressurized air or vacuum at precisely measured values to a catheter 82 that is connected to sensor 10 and communicates with the chamber 13 thereof. The calibrator 80 is preferably a Model PPS-1 Calibrator made by Thermometrics, Inc., of 808 U.S. Highway 1, Edison, N.J. 08817, the assignee of the present invention. Calibrator 80 includes a pressure switch 84 and a vacuum switch 86 for selectively actuating the calibrator to either apply a pressure or a vacuum at an output fitting or outlet 88 thereof, to provide pressurized air or a vacuum through a conduit 90 and coupling unit 91 to the interior of catheter 82. Precision variation of the pressure or vacuum is achieved via a control knob 92 that is suitably coupled to the pressure and vacuum sources. A temperature-regulated heat sink or well 94 is also provided on the calibrator 80. The sensor 10 may be placed into the heat sink 94 in order to check the initial calibration of the sensor at a known temperature, preferably 37 degrees centigrade, at atmospheric pressure. A digital temperature readout device 96, and a manometer 98 calibrated in millimeters of mercury, are employed for providing precise readings of the values of the temperature of heat sink 94 and of the pressure or vacuum at output fitting 88, respectively. The cable 42, which interconnects sensor gage element 20 with the Wheatstone bridge circuitry 44, passes from the pressure sensor 10 through the interior of catheter 82 and through the wall of the coupling unit 91 to the circuitry 44. The passage of cable 42 through the wall of coupling unit 91 is via wires or terminals that are hermetically sealed t the wall in order to avoid leakage of air through the unit at this point.

The meter instrument 70 is preferably one or the other of the following pressure monitors:

A. An HP Model 78205 pressure monitor made by Hewlett Packard Corporation of West 120 Century Road, Paramus, N.J. 07652 or B. An E for M 2200 Series Pressure Monitor made by the Electronics for Medicine Division of Pittsburgh Plate Glass Company of 1 Campus Drive, Pleasantville, N.Y. 10570.

Recalling that the zero adjust control 72 and gain adjust control 74 of meter instrument 70 have already been adjusted as part of the initial calibration procedure, as described earlier herein, and recalling that the pressure responsive element 24 is pre-stressed to insure that the force transmitting member 25 is always in contact with and applying an initial strain to the piezoresistive leg element 34, the initial, in vitro calibration procedure in accordance with the method of the invention continues as follows. With the outside of the pressure responsive element 24 exposed to atmospheric pressure in the heat sink 94 of calibrator 80, a back pressure $P_R$ greater than atmospheric pressure is applied to internal chamber 13 via catheter 82, which is connected to the end 19 of housing 12, and a record is made of the back pressure $P_{Ro}$ that corresponds to the point at which separation of the force transmitting member 25, either from the piezoresistive leg element 34 (if the force transmitting member is adhered to the pressure responsive element 24) or from the pressure responsive element 24 (if the force transmitting member is adhered to the piezoresistive leg element only), occurs. This zero reference back pressure value $P_{Ro}$ is defined as the value for which the initial strain on the piezoresistive leg element 34 disappears (i.e., goes to zero).

After the initial in vitro calibration procedures described above have been completed, the sensor 10 may be inserted into the blood stream of a biological subject and positioned at a site at which in vivo measurements are to be made of pressure and temperature. When it is subsequently desired to check the calibration of the pressure sensor 10 and meter instrument 70, the calibration can be checked without removing the sensor from its in vivo measurement site by using the following procedure:

(i) Observe the pressure value $P_D$ displayed on the meter instrument 70 when the internal chamber 13 of the housing 12 is at atmospheric pressure. This pressure value $P_D$ represents the sum of the ambient pressure surrounding the in vivo location of the sensor 10 and any variations due to drift.

(ii) Slowly increase the back pressure $P_R$ in chamber 13 above atmospheric pressure and observe the displayed value $P_D$ slowly decreasing. Continue slowly increasing the back pressure $P_R$ until the displayed value $P_D$ stops decreasing and record the value of the back pressure $P_{Rc}$ that corresponds to this point (i.e., the value of the back pressure that is applied when the prestressing of the pressure responsive element 24 has just been completely relieved from the piezoresistive leg element 34). Alternatively, the back pressure $P_R$ could be increased to a point beyond the point at which the displayed value $P_D$ stops decreasing, and then the back pressure could be slowly decreased until the displayed value $P_D$ just starts increasing to get the desired back pressure value $P_{Rc}$.

(iii) Subtract from the value of $P_{Rc}$ obtained in step (ii), above, the value of the zero reference back pressure $P_{Ro}$ obtained during the initial in vitro calibration, referred to earlier, to obtain the true differential pressure $P_{Dt}$, and compare the value of $P_{Dt}$ so obtained with the value of $P_D$ observed in step (i) above. If the values of $P_{Dt}$ and $P_D$ compared in this step (iii) are in substantial agreement, the pressure sensor 10 and meter instrument 70 can be assumed to be in calibration and, thus, recalibration thereof is not required. On the other hand, if such values are not in substantial agreement, the pressure sensor 10 and meter instrument 70 can be assumed to be out of calibration, and recalibration in accordance with the following should be undertaken.

(iv) Apply two different back pressures or vacuums $P_{R1}$ and $P_{R2}$, each of which back pressures is less than the value of $P_{Rc}$ and one of which may be atmospheric pressure, to the internal chamber 13 of the pressure sensor 10. Observe the corresponding pressures $P_{D1}$ and $P_{D2}$ displayed on the meter instrument 70 and compute the gain factor G of the instrument 70 by the equation G equals the difference of $P_{D1}$ minus $P_{D2}$ divided by the difference of $P_{R1}$ minus $P_{R2}$. This value of the gain factor G will typically be in the range of from 0.95 to 1.0.

(v) Return the back pressure in chamber 13 to atmospheric pressure and observe the displayed in vivo pressure $P_D$. If no significant change has occurred from the value of $P_D$ observed in step (i), above, adjust the gain control 74 to obtain a new displayed pressure $P_{Dn}$ given by the equation $P_{Dn}$ equals the displayed pressure $P_D$ obtained in this step (v) divided by the gain G obtained in step (iv) immediately above.

(vi) Adjust the zero adjustment control 72 so that the new displayed pressure $P_{Dn}$ is equal to the true differential pressure $P_{Dt}$ determined in step (iii), above.

(vii) If the displayed in vivo pressure $P_D$ observed in step (v) above has changed significantly from the value of $P_D$ observed in the initial in vivo pressure check of step (i) earlier, instead of adjusting the gain control to obtain a new displayed pressure $P_{Dn}$ as called for in step (v) above, slowly increase the back pressure $P_R$ until the displayed value stops decreasing, record the new back pressure value $P_{Rcn}$ corresponding to this point, and subtract the value of $P_{Ro}$, which was obtained during the initial in vitro calibration, from $P_{Rcn}$ to obtain a new true differential pressure $P_{Tn}$ (Note that the displayed pressure $P_D$ at any given time is equal to the gain factor G times the sum of the true pressure differential $P_T$ or $P_{Tn}$ plus the zero offset Z).

(viii) Adjust the gain control 74 to obtain a new displayed pressure $P_{Dn}$ given by the equation $P_{Dn}$ equals the displayed pressure $P_D$ obtained in step (v), above, divided by the gain factor G obtained in step (iv). (In effect, the gain is adjusted to make the gain factor G, as determined in step (iv), unity. This can be verified if necessary by repeating step (iv) after the gain adjustment is made).

(ix) Adjust the zero adjustment control 72 so that the new displayed pressure $P_{Dn}$ is made equal to the true differential pressure $P_{Tn}$ determined from step (vii), above. The sensor 10 and meter instrument 70 are now in calibration and the corrected value of displayed pressure $P_{Dn}$ is given by the equation $P_{Dn} = P_D/G - Z$, where $P_D$ is the uncalibrated displayed pressure observed in step (vii), G is the gain factor obtained in step (iv), and Z is the amount of zero offset introduced in step (ix) to make $P_{Dn} = P_{Tn}$.

It will be apparent from the foregoing description that an improved pressure sensor is provided by the present invention, which pressure sensor permits calibration of its zero offset due to drift while the pressure sensor is located at an in vivo measurement site. In addition, the present invention provides improved methods for checking the calibration of a pressure sensor, and the meter and electrical circuitry associated therewith, and for recalibrating the same as necessary while the pressure sensor remains in such in vivo measurement site.

While there have been shown and described what are presently considered to be the preferred embodiments of this invention, it will be obvious to those skilled in the art that various changes and modifications may be made without departing from the broader aspects of this invention. It is, therefore, aimed in the appended claims to cover all such changes and modifications as fall within the true spirit and scope of this invention.

What is claimed is:

1. A method of checking the calibration of an in vivo pressure sensor, comprising the steps of
   A. Providing a pressure sensor including a housing having an internal chamber, said pressure sensor including a pressure responsive element having inner and outer sides exposed respectively to pressure conditions in said internal chamber and to ambient conditions outside of said housing, a piezoresistive element positioned in said chamber, means coupling said pressure responsive element and said piezoresistive element in such a manner that when equal pressures are applied to opposite sides of said pressure responsive element, said pressure responsive element applies a predetermined load to said piezoresistive element and when unequal pressures are applied to opposite sides of said pressure responsive element, the load applied by said pressure responsive element to said piezoresistive element correspondingly changes, said pressure sensor further including conduit means in communication with said internal chamber and leading to a location remote from said chamber, and circuit means connected to said piezoresistive element and leading to a location remote from said chamber;
   B. Providing meter means having a zero adjustment control in circuit with said circuit means;
   C. Prior to inserting said pressure sensor into an in vivo environment,
      (i) exposing both sides of said pressure responsive element to a common pressure source and setting said zero adjustment control so that said meter means reads zero pressure output,
      (ii) applying a gradually increasing back pressure $P_R$ to said internal chamber while applying atmospheric pressure to the outer side of said pressure responsive element to reduce said predetermined load to zero, and recording the back pressure reading $P_{Ro}$ at which the output of said meter means stops decreasing,
   D. Inserting said pressure sensor into an in vivo environment and
      (i) observing the pressure value $P_D$ displayed on the meter means with the back pressure $P_R$ equal to atmospheric pressure or another known pressure,
      (ii) slowly increasing the back pressure $P_R$ until the displayed value $P_D$ stops decreasing and then recording the back pressure value $P_{Rc}$ corresponding to this point,
      (iii) subtracting the value of $P_{Ro}$ from the value of $P_{Rc}$ obtained in step C(ii) above to obtain the true differential pressure $P_{Dt}$ and comparing the value of $P_{Dt}$ so obtained with the value of $P_D$ obtained in step D(i) above, whereby, if the values of $P_{Dt}$ and $P_D$ compared in step D(iii) are in substantial agreement, the pressure sensor and meter means can be assumed to be in calibration and, if such values are not in substantial agreement, the pressure sensor and meter means can be assumed to be out of calibration.

2. A method of checking the calibration of an in vivo pressure sensor according to claim 1, wherein said pressure responsive element comprises a flexible diaphragm, wherein said meter means includes a gain control in circuit with said circuit means at said remote location, and further including, after step C(i) but prior to inserting said pressure sensor into said in vivo environment, the steps of applying atmospheric pressure to said internal chamber, applying a known value of pressure to the outer side of said diaphragm, and adjusting said gain control to provide a displayed value on said meter means equal to said known value of pressure.

3. A method of checking the calibration of an in vivo pressure sensor according to claim 2, and, if the values of $P_{Dt}$ and $P_D$ compared in step D(iii) thereof are not in substantial agreement, recalibrating said pressure sensor by performing the further steps of E. Applying two different back pressures or vacuums $P_{R1}$ and $P_{R2}$, each of which is less than the value of $P_{Rc}$ and one of which may be atmospheric pressure, to the internal chamber of said pressure sensor, observing the corresponding pressures $P_{D1}$ and $P_{D2}$ displayed on the meter means, and computing the gain factor G by the equation G equals the difference of $P_{D1}$ minus $P_{D2}$ divided by the difference of $P_{R1}$ minus $P_{R2}$;

F. Returning the back pressure in said internal chamber to atmospheric pressure if it is not already there, observing the resulting displayed pressure $P_D$, adjusting the gain control to obtain a new displayed pressure $P_{Dn}$ given by the equation $P_{Dn}$ equals the displayed pressure $P_D$ obtained in this step F divided by the gain G obtained in step E: and, G. Adjusting the zero adjustment control so that the new displayed pressure $P_{Dn}$ is made equal to the true differential pressure $P_{Dt}$ determined from step D(iii).

4. A method of checking the calibration of an in vivo pressure sensor according to claim 2, and, if the values of $P_{Dt}$ and $P_D$ compared in step D(iii) thereof are not in substantial agreement, recalibrating said pressure sensor by performing the further steps of E. Applying two different back pressures or vacuums $P_{R1}$ and $P_{R2}$, each of which is less than the value of $P_{Rc}$ and one of which may be atmospheric pressure, to the internal chamber of said pressure sensor, observing the corresponding pressures $P_{D1}$ and $P_{D2}$ displayed on the meter means, and computing the gain factor G by the equation G equals the difference of $P_{D1}$ minus $P_{D2}$ divided by the difference of $P_{R1}$ minus $P_{R2}$;

F. Observing the displayed in vivo pressure $P_D$ with the back pressure at atmospheric pressure and, if a significant change has occurred from the value of $P_D$ observed in step D(i), slowly increasing the back pressure $P_R$ until the displayed value stops decreasing, recording the new back pressure value $P_{Rcn}$ corresponding to this point, and subtracting the value of $P_{Ro}$ obtained in step C(ii) from $P_{Rcn}$ to obtain a new true differential pressure $P_{Tn}$;

G. Adjusting the gain control to obtain a new displayed pressure $P_{Dn}$ given by the equation $P_{Dn}$ equals the displayed pressure $P_D$ obtained in step F divided by the gain G obtained in step E; and, H. Adjusting the zero adjustment control so that the new displayed pressure $P_{Dn}$ is made equal to the true differential pressure $P_{Tn}$ determined from step F.

* * * * *

UNITED STATES PATENT AND TRADEMARK OFFICE
CERTIFICATE OF CORRECTION

PATENT NO. : 4,886,070

DATED : December 12, 1989

INVENTOR(S) : Philip C. Demarest

It is certified that error appears in the above-identified patent and that said Letters Patent is hereby corrected as shown below:

IN THE ABSTRACT

Line 10 "interanl" should read --internal--.

Line 12, after "releasably" insert -- coupling the pressure responsive element of the piezore- --.

Line 18 "thre" should read --the--.

Line 22 "fo" should read --of--.

Signed and Sealed this

Twelfth Day of March, 1991

*Attest:*

HARRY F. MANBECK, JR.

*Attesting Officer*      *Commissioner of Patents and Trademarks*